United States Patent
Hsieh et al.

(10) Patent No.: US 10,159,741 B2
(45) Date of Patent: Dec. 25, 2018

(54) METHODS AND COMPOSITIONS COMPRISING HYALURONAN FOR ENHANCING BONE MARROW CELL THERAPY

(71) Applicant: National Cheng Kung University, Tainan (TW)

(72) Inventors: Ching Ho Hsieh, Tainan (TW); Chien Hsi Chen, Tainan (TW); Shoei Shen Wang, Taipei (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 13/777,139

(22) Filed: Feb. 26, 2013

(65) Prior Publication Data

US 2013/0315878 A1   Nov. 28, 2013

Related U.S. Application Data

(60) Provisional application No. 61/651,604, filed on May 25, 2012.

(51) Int. Cl.
| | | |
|---|---|---|
| *A61K 35/28* | (2015.01) | |
| *A61K 47/36* | (2006.01) | |
| *A61L 27/20* | (2006.01) | |
| *A61L 27/38* | (2006.01) | |

(52) U.S. Cl.
CPC .............. *A61K 47/36* (2013.01); *A61K 35/28* (2013.01); *A61L 27/20* (2013.01); *A61L 27/3834* (2013.01); *A61L 2430/20* (2013.01)

(58) Field of Classification Search
CPC ............... A61K 2300/00; A61K 35/28; A61K 2035/124; A61L 2430/20; A61L 27/38; A61L 27/3804
USPC ......................................................... 424/93.7
See application file for complete search history.

(56) References Cited

U.S. PATENT DOCUMENTS

| | | | |
|---|---|---|---|
| 7,470,538 B2 * | 12/2008 | Laughlin et al. | 435/325 |
| 8,038,991 B1 * | 10/2011 | Stankus et al. | 424/93.7 |
| 2009/0291061 A1 * | 11/2009 | Riordan et al. | 424/85.2 |

OTHER PUBLICATIONS

Walpole et al., The weight of nations: an estimation of adult human biomass. BMC Public Health, vol. 12 (2012) pp. 1-6.*

Taylor et al., Glycosaminoglycans and their proteoglycans: host-associated molecular patterns for initiation and modulation of inflammation. The FASEB Journal, vol. 20, No. 1 (Jan. 2006) pp. 9-22.*

* cited by examiner

*Primary Examiner* — Kara D Johnson

(57) ABSTRACT

Disclosed herein are methods and compositions for treating cardiovascular disease and damaged cardiac tissue which employ at least one hyaluronan (HA) compound and one or more cells selected from the group consisting of stem cells, precursor cells, progenitor cells, committed cells, mature somatic cells, and recombinant cells.

11 Claims, 12 Drawing Sheets

METHODS AND COMPOSITIONS COMPRISING HYALURONAN FOR ENHANCING BONE MARROW CELL THERAPY

CROSS-REFERENCE TO RELATED APPLICATIONS

This application claims the benefit of U.S. Application Ser. No. 61/651,604, filed 25 May 2012, which is herein incorporated by reference in its entirety.

BACKGROUND OF THE INVENTION

1. Field of the Invention

The present invention relates to methods and compositions for treating cardiovascular disease and damaged cardiac tissue.

2. Description of the Related Art

Coronary artery disease (CAD) is the most common type of heart disease. CAD occurs when the coronary arteries become narrow as a result of atherosclerosis (Hansson G K. N Engl J Med. 2005; 352:1685-95). In CAD, the blood flow that supplies the heart muscle is decreased, which further leads to myocardial infarction (MI) and scar formation (Strauer B E, et al. Circulation. 2002; 106:1913-8). Unfortunately, the standard treatments including early revascularization using coronary intervention followed with supported pharmaceutical administration (Malik F I, et al. Science. 2011; 331:1439-43) are not sufficient. Eventually, accumulated cardiomyocyte loss contributes to heart failure. The American Heart Association has estimated that there are about 6 million patients with heart failure in the United States each year (Go A S, et al. Circulation. 2013; 127:e5-e245). Therefore, the ultimate goal of CAD treatment is to reduce cardiomyocytes death and to prevent further occurrence of heart failure (Rafii S, et al. Nat. Med. 2003; 9:702-12).

Previous studies have shown that cell therapy is a promising approach for heart repair post-MI (Murry C E, et al. Circulation. 2005; 112:3174-83; and Passier R, et al. Nature. 2008; 453:322-9). Some clinical trials have also demonstrated that autologous stem cell therapy can improve cardiac function after MI. These stem cells can participate in angiogenesis and provide paracrine factors to protect cardiomyocytes from the damage of ischemia. However, the results of these clinical studies remain controversial (Segers V F, et al. Nature. 2008; 451:937-42). The major reason may be that only a small portion of cells can survive and remain in the ischemia region after transplantation (Seeger F H, et al. Nat Clin Pract Cardiovasc Med. 2007; 4 Suppl 1:S110-3). For example, some studies have revealed that more than 90% of cells are lost during intra-myocardial injection due to contraction of the heart while the few resident cells have difficulty surviving in the highly hypoxic condition of the ischemic region (Segers 2008; and Laflamme M A, et al. Nat. Biotechnol. 2005; 23:845-56).

Therefore, a need still exists for cell therapy treatments for repairing damaged cardiac tissues.

SUMMARY OF THE INVENTION

In some embodiments, the present invention is directed to methods of treating a cardiovascular disease or a damaged cardiac tissue in a subject, which comprises administering to the subject at least one HA compound and one or more cells selected from the group consisting of stem cells, precursor cells, progenitor cells, committed cells, mature somatic cells, and recombinant cells. In some embodiments, the cardiovascular disease is coronary artery disease, cardiomyopathy, myocardial infarction, atherosclerosis, heart failure, a congenital heart disease, a valvular heart disease, or a vascular disease such as a peripheral artery occlusive disease, Raynaud's phenomenon, Berger's disease, or vascular inflammation or damage, preferably coronary artery disease, myocardial infarction, atherosclerosis, or a vascular disease. In some embodiments, the damaged cardiac tissue was caused by a trauma thereto, e.g., a myocardial infarction, or a viral infection. In some embodiments, the at least one HA compound and the one or more cells are administered to the subject before, during, and/or after the occurrence of the cardiovascular disease or damage to the cardiac tissue. In some embodiments, the at least one HA compound and the one or more cells are administered in a therapeutically effective amount. In some embodiments, the at least one HA compound and the one or more cells are administered together in the form of a single composition. In some embodiments, the one or more cells are hematopoietic stem cells, mesenchymal stem cells, and/or endothelial stem cells. In some embodiments, the one or more cells are autologous cells to the subject or allogeneic cells from one or more donors. In some embodiments, the one or more cells are myofibroblasts, bone marrow cells, blood cells, adipose tissue-derived cells, placental cells, umbilical cord cells, umbilical cord blood cells, amniotic fluid cells, cardiomyocyte-like cells, pluripotent stem cell-derived cells (e.g., embryonic stem cells or induced pluripotent stem cells) or somatic cell-derived stem/progenitor cells (e.g., a somatic cell de-differentiated into stem/progenitor cell, then re-differentiate into another type of somatic cell such as cardiomyocyte, or direct trans-differentiation from a somatic cell into another type of cell). In some embodiments, the at least one HA compound and the one or more cells are administered to the myocardium of a heart by thoracotomy, cardiac catheterization, echo-guided or endoscope-assisted injection, or a syringe. In some embodiments, the methods further comprise administering at least one supplementary active compound to the subject. Supplementary active compounds such as a protein (e.g., VEGF, PDGF, FGF, IGF, SDF, HGF, BMP, EGF, EPO, GDF, G-CSF, Wnt, angiopoietin, thrombomodulin, etc.), a nucleic acid molecule (e.g., DNA, RNA, etc.), and other synthetic or natural compounds. In some embodiments, the subject is an animal such as a rodent or a pig. In some embodiments, the subject is a human. In some embodiments, the subject is treated during and/or after the myocardial infarction. In some embodiments, the amount of the at least one HA compound is about 0.01 to about 10 mg/kg body weight of the subject, the amount of the one or more cells is about $1\times10^4$ to about $1\times10^8$ per kg body weight of the subject, or both.

In some embodiments, the present invention is directed to compositions for treating a cardiovascular disease or a damaged cardiac tissue, comprising at least one HA compound; and one or more cells selected from the group consisting of stem cells, precursor cells, progenitor cells, committed cells, mature somatic cells, and recombinant cells. In some embodiments, the one or more cells are hematopoietic stem cells, mesenchymal stem cells, and/or endothelial stem cells. In some embodiments, the one or more cells are autologous to a given subject to be treated with the composition or allogeneic cell from one or more donors. In some embodiments, the one or more cells are myofibroblasts, bone marrow cells, blood cells, adipose tissue-derived cells, placental cells, umbilical cord cells, umbilical cord blood cells, amniotic fluid cells, cardiomyocyte-like cells, pluripotent stem cell-derived cells (e.g., embryonic stem cells or induced pluripotent stem cells) or somatic cell-derived stem/progenitor cells (e.g., a somatic cell de-differentiated into stem/progenitor cell, then re-differentiate into another type of somatic cell such as cardiomyocyte, or direct trans-differentiation from a somatic cell into another type of cell). In some embodiments, the cardiovascular disease is coronary artery disease, cardiomyopathy, myocardial infarction, atherosclerosis, heart failure, a congenital heart disease, a valvular heart disease, or a vascular disease such as a peripheral artery occlusive disease, Raynaud's phenomenon, Berger's disease, or vascular inflammation or damage, preferably coronary artery disease, myocardial infarction, atherosclerosis, or a vascular disease. In some embodiments, the damaged cardiac tissue was caused by a trauma thereto, e.g., a myocardial infarction, or a viral infection. In some embodiments, the composition is formulated for administration to the myocardium of a heart by thoracotomy, cardiac catheterization, echo-guided or endoscope-assisted injection, or a syringe. In some embodiments, the compositions further comprise at least one supplementary active compound to the subject. Supplementary active compounds such as a protein (e.g., VEGF, PDGF, FGF, IGF, SDF, HGF, BMP, EGF, EPO, GDF, G-CSF, Wnt, angiopoietin, thrombomodulin, etc.), a nucleic acid molecule (e.g., DNA, RNA, etc.), and other synthetic or natural compounds. In some compositions according to the present invention, the at least one HA compound is up to about 5%, preferably up to about 3%, more preferably up to about 2%, or most preferably about 1% by weight of the composition, and the amount of the one or more cells are about $1 \times 10^4$ to about $1 \times 10^8$ in a single dosage volume of about 100 to about 2000 μL.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 1A shows the quantification of the adhered bone marrow cells in the different coating conditions. Data are presented as the mean±SEM. n=4 per group. The increased fold changes of MNC adhesion by HA are as follows: HA vs. control=19.8×, HA vs. fibronectin=4.6×, HA vs. gelatin=3.3×. FIG. 1B shows the quantification of Ki67-positive cells under the different coating conditions. The increased fold changes of MNC proliferation by HA are as follows: HA vs. control=3.5×, HA vs. fibronectin=2.5×, and HA vs. gelatin=4.2×. The data are presented as the mean±SEM. n=4 per group. **$P<0.01$.

FIG. 2A shows the quantification of MNC vascular differentiation under the different coating conditions. The data are presented as the mean±SEM. n=4 per group. Scar bar: 50 μm. The increased fold changes of MNC Flk-1, vWF and SM22-α expression by HA are as follows: 3.7×, 3.7× and 2.1× compared with control, respectively. FIG. 2B shows the quantitative RT-PCR results that HA promotes the paracrine gene expression profiles of MNCs cultured under hypoxia. FIG. 2C shows the quantification of doxorubicin-induced MNC apoptosis. The data are presented as the mean±SEM. n=4 per group. HA also prevents MNC apoptosis compared with control and other coating conditions by fibronectin or gelatin.

FIG. 4A shows the number of infiltrated neutrophils at the border zone from each group. Data are presented as mean±SEM. $P<0.01$, *$P<0.001$. n=6 per group. The decreased fold changes of neutrophil number by HA/MNC treatment are as follows: 2.4× vs. control, 1.05× vs. HA alone and 1.45× vs. MNC alone. FIG. 4B shows the quantification of infiltrated macrophages in different experimental groups. Data are presented as mean±SEM. *$P<0.05$, $P<0.01$, *$P<0.001$. n=8 per group. The decreased fold change of macrophage number by HA/MNC treatment are as follows: 1.4× vs. control, 1.2× vs. HA alone and 1.08× vs. MNC alone.

FIG. 5A shows histograms depicting the left ventricle ejection fraction (EF %) one day and 28 days post-MI in the sham and other experimental groups. The data are presented as the mean±SEM. *$P<0.05$, ***$P<0.001$. n=8 per group. The recovery percentage of EF % by HA/MNC treatment is about 45%, a significant improvement compared with the recovery rate of 16% by treatment with HA alone or treatment with MNC alone. FIGS. 5B and 5C show the statistical analysis of the echocardiographic results of the left ventricle internal dimensions at diastole (LVIDd, B) and systole (LVIDs, C) in the sham and other treatment groups. HA/MNC treatment prevents ventricular dilatation better than HA alone or MNC alone treatment. The data are presented as the mean±SEM. *$P<0.05$, ***$P<0.001$. n=8 per group. FIG. 5D shows the statistical analysis of scar length in various groups. HA/MNC treatment exerts less scar size (about 17%) than those of control (44%), HA alone (32%) or MNC alone (29%) groups. The data are presented as the mean±SEM. *$P<0.05$, $P<0.01$, *$P<0.001$. n=8 per group.

FIGS. 7A-7B show the quantification of capillary density at the peri-infarct (FIG. 7A) and infarct (FIG. 7B) areas. The data are presented as the mean±SEM. *$P<0.05$. n=8 per group. FIGS. 7C-7D show the quantification of arteriole density at the peri-infarct (FIG. 7C) and infarct (FIG. 7D) areas. The data are presented as the mean±SEM. *$P<0.05$, ***$P<0.001$. n=8 per group. Compared with controls, HA/MNC treatment improves capillary density at the peri-infarct by about 2× and at the infarct by about 4.2×, and improves arteriole density at the peri-infarct by about 3.3× and at the infarct by about 2.8×.

FIG. 9A shows an illustration of study time course including MNC labeling, injection, echocardiography, coronary artery ligation, catheterization, and sacrifice. FIG. 9B shows histograms depicting the left ventricle ejection fraction one day, one month, and two months post-MI in the sham and other experimental groups. Data are presented as mean±SEM. *P<0.05, ***P<0.001. n=7 per group. The recovery percentage of EF % at 2 months by HA/MNC treatment in pigs is about 38%, a significant improvement compared with the recovery rate of 7% by HA alone or 11% by MNC alone treatment. FIGS. 9C and 9D show the statistical analysis of the echocardiographic results of the interventricular thickness at diastole (FIG. 9C) and systole (FIG. 9D) in the sham and other treatment groups. *P<0.05, **P<0.01. n=7 per group. HA/MNC treatment prevents ventricular dilatation better than treatment with HA alone or treatment with MNC alone.

Figure 1A:
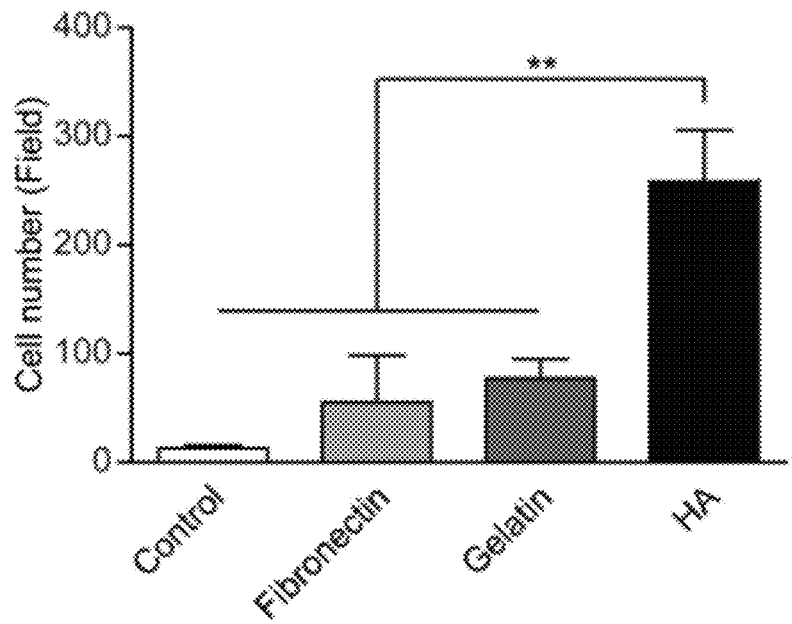
FIGS. 1A-1B show that HA promotes adhesion and proliferation of bone marrow mononuclear cells (MNCs) in culture.

Color copies of these figures can be obtained from Chen C H et al. "Hyaluronan Enhances Bone Marrow Cell Therapy for Myocardial Repair after Infarction." Molecular Therapy. 2013 Jan. 8, which is herein incorporated by reference in its entirety. See also HyperTextTransferProtocol://WorldWideWeb.nature.com/mt/journal/vaop/ncurrent/full/mt2012268a.HyperTextMarkupLanguage, wherein HyperTextTransferProtocol=http, WorldWideWeb=www, and HyperTextMarkupLanguage=html.

DETAILED DESCRIPTION OF THE INVENTION

The present invention provides compositions comprising at least one hyaluronan compound and one or more bone marrow mononuclear cells (MNCs) and methods of using the compositions to treat cardiac tissues. According to the present invention, MNCs include hematopoietic stem cells, mesenchymal stem cells, endothelial stem cells, and blood cells, and cells that can replace the MNCs such as amniotic fluid cells, placental cells, cord or cord blood cells, embryonic stem cells or induced pluripotent stem cells or their progeny, myoblasts, and cardiac stem cells. The one or more MNCs may be obtained from allogenic or autogenic sources and/or recombinant methods known in the art. For example, mesenchymal stem cells (MSCs) may be isolated from the bone marrow, adipose tissues, placenta, or umbilical cord or donor sources, hematopoietic stem cells (HSCs) may be isolated from the bone marrow or peripheral blood, and cardiac stem cells may be isolated from the bone marrow or heart tissue, from one or more donor subjects or from the subject to be treated.

Hyaluronan (HA) is a non-sulfated glycosaminoglycan and a natural component of the extracellular matrix of cells. Hyaluronan (also known as hyaluronic acid or hyaluronate) can be isolated from natural sources or obtained from commercial vendors. As used herein, the term "hyaluronan compound" (HA compound) refers to a plurality of repeating disaccharide units of N-acetylglucosamine and D-glucuronic acid, and derivatives thereof. Derivatives of hyaluronan include hyaluronan esters, adipic dihydrazide-modified hyaluronan, hyaluronan amide products, cross-linked hyaluronic acid, hemiesters of succinic acid or heavy metal salts of hyaluronic acid, partial or total esters of hyaluronic acid, sulphated hyaluronic acid, N-sulphated hyaluronic acid, and amine- or diamine-modified hyaluronic acid. Hyaluronan compounds also include composites of hyaluronan and silk, cross-linked hyaluronan or other natural or synthetic materials. Hyaluronan derivatives can be obtained by chemically modifying one or more functional groups (e.g., carboxylic acid group, hydroxyl group, reducing end group, N-acetyl group) of hyaluronan or hyaluronic acid and/or crosslinking hyaluronan with other molecules using methods known in the art. In some embodiments, the HA compound has a molecular weight up to about 1640 kDa. In some embodiments, the at least one HA compound may be provided as a mixture with another biopolymer such as collagen, gelatin, alginate, chitosan, fibronectin, fibrin glue, and the like.

In some embodiments, the at least one HA compound is provided in the form of a hydrogel. As used herein, a "hydrogel" is a composition, which may be natural or synthetic, having a highly hydrated property that is similar to natural tissues and may be employed as a pharmaceutically acceptable vehicle or carrier for the one or more MNCs. The hydrogels according to the present invention may further include alginate (Landa N, et al. Circulation. 2008; 117:1388-96), collagen (Flanagan T C, et al. Biomaterials. 2006; 27:2233-46), extracellular matrix emulsion (Zhao Z Q, et al. J Am Coll Cardiol. 2010; 55:1250-61), fibrin glue (Christman K L, et al. J Am Coll Cardiol. 2004; 44:654-60), Matrigel (Kofidis T, et al. J Thorac Cardiov Sur. 2004; 128:571-8), and self-assembling peptides (Davis M E, et al. Circulation. 2005; 111:442-50; U.S. Pat. No. 5,670,483; U.S. Pat. No. 6,548,630; and U.S. Pat. No. 7,429,567). A hydrogel according to the present invention may be made using methods known in the art. See, for example, US 20120064150, US 20110150823, US 20050281880, US 20040185086, and the like.

Hydrogels according to the present invention are biocompatible, and preferably have little to no immunogenicity, in the subject to be treated. As used herein, a "biocompatible" material is one that does not have any significant toxic or injurious effects or elicit any significant undesirable local or systemic effects in a given biological system. Thus, suitable hydrogels according to the present invention do not have any significant toxic or injurious effects or elicit any significant undesirable local or systemic effects in the subjects to be treated. As used herein, "little to no immunogenicity" means slightly induces or does not induce immune response in the given subject. In some embodiments, the hydrogels do not detrimentally alter the in vitro and/or in vivo biological activity and function of any MNCs and therapeutic molecules present in the compositions. In some embodiments, the hydrogels are also biodegradable. As used herein, "biodegradable" means the given material is capable of being absorbed by the human body.

The compositions according to the present invention may further include one or more supplementary active compounds the therapeutic molecules which include biomolecules such as peptides, proteins (such as vascular endothelial growth factor (VEGF), platelet-derived growth factor (PDGF), a fibroblast growth factor (FGF), an insulin-like growth factor (IGF), a stromal cell-derived factor (SDF), hepatocyte growth factor (HGF), a bone morphogenetic protein (BMP), epidermal growth factor (EGF), erythropoietin (EPO), a growth differentiation factor (GDF), granulocyte colony-stimulating factor (G-CSF), a Wnt, angiopoietin and thrombomodulin), DNAs, RNAs, plasmids, and the like, and chemical compounds.

In some embodiments, the compositions are formulated to be injected into the myocardium of a subject in need thereof, e.g., a subject having an infarcted myocardium. In these embodiments, the amount of the at least one HA compound should not inhibit the composition from being drawable with a given syringe for injection. It is noted that the ability an HA compound to be drawn through a given syringe may also be influenced by the molecular weight of the HA compound and/or the presence of other components in the composition as well as the gauge of the syringe. Thus, as an example, the amount of the at least one HA compound having a molecular weight of about 1640 kDa in a composition to be injected using syringe having a 27-29 sized gauge and the HA compound is up to about 1% by weight of the total composition.

As demonstrated in the experiments herein, HA promotes MNC adhesion, survival and proliferation, paracrine factor associated genes expression, and endothelial and smooth muscle cell differentiation. In addition, the compositions according to the present invention significantly improve cardiac function via multiple mechanisms including enhanced angiogenesis, arteriogenesis, and increased cardiomyocyte survival, and reduce scar formation post-myocardial infarction in treated subjects. In particular, intramyocardial injection of a composition according to the present invention comprising both HA and MNCs improved heart function, reduced cardiomyocytes loss and scar formation at the early stage and 28 or 56 days post-myocardial infarction (post-MI) and promoted angiogenesis and arteriogenesis after myocardial infarction (MI) in animal models. Further, HA was found to provide a microenvironment which retains the MNCs therein at the site of administration. Moreover, most of the newly formed vessels were DiI negative and part of the injected MNCs differentiated into vessel cells and became integrated into pre-existing vessels. Thus, the combined administration of at least one HA compound and one or more MNCs results in the recruitment of host endothelial cells and smooth muscle cells to the site of administration, e.g., infarct site being treated, and helps the formation of new vessel cells and structures.

In summary, treatment with at least one HA compound and one or more MNCs (HA/MNC treatment) results in:
  Greater adhesion and proliferation of the MNCs
  Increased secretion of protective paracrine factors including basic fibroblast growth factor (FGF-2), HGF, insulin-like growth factor 1 (IGF-1), platelet-derived growth factor subunit B (PDGFb) and stromal cell-derived factor-1 (SDF-1) by the MNCs
  Decreased apoptosis of the MNCs and cardiomyocytes
  Increased angiogenesis and arteriogenesis
  Reduced inflammatory response
  Increased cardioprotection and cardiac function
  Decreased scar tissue formation and collagen accumulation in cardiac tissues
  Increased integration of MNCs into vessels Therefore, the present invention also provides methods of treating a subject having damaged cardiac tissue, trauma to one or more cardiac tissues, and/or cardiovascular diseases and methods of inhibiting and/or reducing the amount of damaged or scarred cardiac tissue in subjects which comprises administering the at least one HA compound and one or more MNCs to the subject. As used herein, "a cardiovascular disease" refers to heart diseases such as coronary artery disease (CAD), cardiomyopathy, myocardial infarction, ischemia, atherosclerosis, heart failure, congenital heart diseases, valvular heart diseases, ischemic heart diseases, and other conditions which damage the heart tissue such as viral infection or trauma, and vascular diseases such as peripheral artery occlusive diseases, Raynaud's phenomenon, Berger's disease, and other connective tissue disorder associated vascular inflammation or damage. As used herein, "cardiac tissue" refers to one or more tissues (e.g., endocardium, myocardium, and epicardium) and cells (e.g., cardiomyocytes, cardiac fibroblasts, endothelial cells, and vascular smooth muscle cells) of a heart, preferably a mammalian heart, more preferably a human heart. The at least one HA compound and the one or more MNCs may be administered to the cardiac tissue before, during, and/or after the onset of the cardiovascular disease or trauma, e.g., surgery, which will likely result in damage to the cardiac tissue if left untreated. In some embodiments, the at least one HA compound and the one or more MNCs are injected into the cardiac tissue to be treated. The injection routines include (1) epicardial injection by surgical, echo-guided or endoscope-assisted approach or (2) transendocardial injection by a catheter or during open heart surgery. In some embodiments, the at least one HA compound and the one or more MNCs are applied directly on the cardiac tissue to be treated, e.g., during open heart surgery. In some embodiments, the at least one HA compound and the one or more MNCs are administered concurrently, but as separate compositions. In some embodiments, the at least one HA compound and the one or more MNCs are administered together in the form of a single composition.

In some embodiments, the at least one HA compound and/or the one or more MNCs are administered in a therapeutically effective amount. As used herein, a "therapeutically effective amount" is the amount of the at least one HA compound and the one or more MNCs which result in the desired therapeutic effect (e.g., greater adhesion and proliferation of the MNCs, increased secretion of protective paracrine factors including FGF-2, HGF, IGF-1, PDGFb and SDF-1 by the MNCs, decreased apoptosis of the MNCs and cardiomyocytes, increased angiogenesis and arteriogenesis, reduced inflammatory response, increased cardioprotection and cardiac function, decreased scar tissue formation and collagen accumulation in cardiac tissues, and/or increased integration of MNCs into vessels) as compared to a control such as a placebo. A therapeutically effective amount may be readily determined by standard methods known in the art. The dosages to be administered can be determined by one of ordinary skill in the art depending on the clinical severity of the condition to be treated and the age and weight of the subject. Preferred therapeutically effective amounts of HA range from about 0.01 to about 10 mg/kg body weight. Preferred therapeutically effective amounts of MNCs range from about $1\times10^4$ to about $1\times10^8$ per kg body weight. In some embodiments, the composition according to the present invention comprises up to about 5%, preferably up to about 3%, more preferably up to about 2%, or most preferably about 1% by weight of the at least one HA compound and about $1\times10^4$ to about $1\times10^8$ of the one or more MNCs in about 100-2000 µL. In the experiments below, 200 µL of 1% HA and $1\times10^6$ MNCs was found to be therapeutically effective in rat models and 2 ml of 1% HA and $1\times10^8$ MNCs were found to be therapeutically effective in pig models. One skilled in the art may readily determine the therapeutically effective amounts for human subjects using the methods described herein and/or drawing correlations from these animal models.

Treatment of a subject with the at least one HA compound and the one or more MNCs according to the present invention can include a single treatment or a series of treatments. It will be appreciated that the actual dosages will vary according to the particular composition, the particular formulation, the mode of administration, and the particular subject and condition being treated. It will also be appreciated that the effective dosage used for treatment may increase or decrease over the course of a particular treatment. Optimal dosages for a given set of conditions may be ascertained by those skilled in the art using conventional dosage-determination tests in view of the experiments herein. Changes in dosage may result and become apparent by standard diagnostic assays known in the art.

The pharmaceutical compositions of the invention may be prepared in a unit-dosage form appropriate for the desired mode of administration. The compositions of the present invention may be administered for therapy by (1) epicardial injection through surgical, echo-guided or endoscope-assisted approach or (2) transendocardial injection through a catheter or during open heart surgery. It will be appreciated that the preferred route will vary with the condition and age of the subject, the nature of the condition to be treated, and the given composition.

In addition to the at least one HA compound, the compositions of the present invention may further comprise an inert, pharmaceutically acceptable carrier or diluent. As used herein the language "pharmaceutically acceptable carrier" is intended to include any and all solvents, dispersion media, coatings, antibacterial and antifungal agents, isotonic and absorption delaying agents, and the like, compatible with pharmaceutical administration and known in the art. Except insofar as any conventional media or agent is incompatible with the active compound, use thereof in the compositions is contemplated.

The present invention also provides kits comprising at least one HA compound and the one or more MNCs provided as a single mixture or in separate packaging such that the at least one HA compound and the one or more MNCs may be mixed together by the user. The kits may comprise the at least one HA compound and/or the one or more MNCs as a single dose or as multiple doses. The kits may further include reagents, devices, instructional material, or a combination thereof. For example, the kits may include devices for mixing the at least one HA compound and the one or more MNCs together and/or administering the at least one HA compound and the one or more MNCs to a subject. In clinical treatment methods where the one or more MNCs are be freshly isolated from the bone marrow of the donor just prior to administration to the subject being treated. Thus, in some embodiments, the kits comprise the at least one HA compound and reagents and/or devices for isolating the one or more MNCs from the donor, mixing the donor MNCs with the at least one HA compound, and/or administering the donor MNCs in conjunction with the at least one HA compound.

The following examples are intended to illustrate but not to limit the invention.

Materials and Methods
Preparation of Different Coating Plates

Non-coating tissue culture plate served as the control. Fibronectin (Millipore) was diluted with phosphate buffer saline (PBS) for 1% fibronectin solution. Gelatin powder was dissolved in double distilled water (ddH$_2$O) for 1% (w/v) solution and sterilized. Hyaluronan (HA) powder (1630 kDa; Sigma-Aldrich) was dissolved in PBS at 4° C. for at least 24 hours to form 1% (w/v) HA solution. Tissue culture plates were coated with all three solutions for at least 1 hour at 37° C.

Bone Marrow Mononuclear Cell Isolation, Purification and Culture

MNCs cells were isolated from the femoral bone of normal adult male Sprague-Dawley rats (200-250 g; 5-6 weeks old) or from the anterior tibia of sexually mature Lanyu mini-pigs of either sex (about 5 months old, body weight 23.8±0.6 kg). The cells were flushed by 10% FBS/HBSS solution from femoral bone and purified by Histopaque®-1077 (Sigma-Aldrich, St. Louis, Mo.) to remove the red blood cells. These cells were washed by 10% FBS/HBSS solution three times and cultured in alpha-MEM medium containing 10% fetal bovine serum (FBS) (Gibco brand of Life Technologies, Carlsbad, Calif.) or Endothelial Basal Medium 2 (Lonza, Walkersville, Md.).

Bone Marrow Mononuclear Cell Adhesion, Proliferation and Gene Expression

MNCs were cultured on 6-well plates without additional coating as control, other wells coated with 1% fibronectin, 1% gelatin or 1% HA and then maintained at 37° C., 5% CO$_2$ incubator for 24 hours. After 24 hours, all cells were fixed with 4% paraformadyhyde, then were treated with 0.1% triton X-100 to increase cell permeability and were stained with 4',6-diamidino-2-phenylindole fluorescent dye (DAPI). Total cell number was counted by high throughput screening microscopy (ImageXpress®, Molecular Devices, Sunnyvale, Calif.) and analyzed by MetaXpress® software (Molecular Devices). The proliferating cells were measured by Ki67 (GeneTex, Inc., San Antonio, Tex.) staining. The hypoxia condition was induced in a hypoxia chamber with 5% $CO_2$ and nitrogen to decrease oxygen concentration. MNCs were cultured in the hypoxia chamber for 2 days. The total RNA of MNC was extracted using TRIzol® (Invitrogen brand of Life Technologies, Carlsbad, Calif.) and the RNA was converted to cDNA using RevertAid™ Reverse Transcriptase (Fermentas GmbH, St. Leon-Rot, DE). The paracrine factor associated genes expression pattern were measured by real time PCR.

Bone Marrow Mononuclear Cells Apoptosis Analysis

Freshly isolated MNCs were cultured on 10 cm culture plates with or without coating with 1% fibronectin, 1% gelatin and 1% HA and then maintained at 37° C., 5% $CO_2$ incubator overnight. The next day, 5 µM doxorubicin was added to the medium to induce cell apoptosis. After 5 hours, cells were harvested and stained with propodium iodide (Sigma-Aldrich) to quantify the cell apoptosis using flow cytometry.

Tissue Protein Isolation

The heart from different treatment groups were harvested two days after coronary artery ligation. The ischemia region was cut out and the tissue was stored in liquid nitrogen. The frozen tissue was added with TRIzol® (Invitrogen) and homogenized for 10 to 20 seconds on ice. The total RNA was extracted and converted into cDNA for gene expression analysis.

Experimental Animals

All animal protocols were approved by the Institutional Animal Care and Use Committee at National Cheng Kung University. Adult male SD rats (6 weeks old, weight 200-250 g) acquired from the National Cheng Kung University Animal Center were used. Rats were anesthetized with Zoletil and Ronpum before surgery and sacrifice. For large animal tests, sexually mature Lanyu mini-pigs of either sex (about 5 months old, body weight 23.8±0.6 kg) from the National Tai-tung Animal Propagation Station were used. Anesthesia was given to all pigs before surgery and in vivo measurements. After an overnight fast, the pigs were induced with Zoletil (12.5 mg/kg; Virbac, France), Rompun (0.2 ml/kg; Bayer Healthcare, Germany), and atropine (0.05 mg/kg; TBC, Taiwan) before intubation. They were attached to a respirator for intermittent positive pressure ventilation with a mixture of oxygen, air, and Isoflurane (1.5 to 2%; Baxter Healthcare, Guayama, PR). An indwelling needle was placed in an ear vein for continuous administration of saline and anesthetic drugs, if necessary. After surgery, analgesics (Keto; YSP, Taiwan) and antibiotics (Ampolin; YSP, Taiwan) were administered to relieve pain and prevent infection.

Autologous Bone Marrow Mononuclear Cell Isolation and DiI Labeling

The pigs were placed in the supine position, and 20 ml of bone marrow was aspirated from beneath the tibial tuberosity and stored in a syringe containing 2500 IU of heparin (Braun, Germany). The bone marrow aspirate was diluted to 1:1 with Hank's buffered salt solution (HBSS) containing 5% fetal bovine serum (FBS), passed through a 70 µm strainer, and then processed by density-gradient centrifugation (Ficoll-Paque Premium; GE Healthcare) to exclude erythrocytes and granulocytes. MNCs were collected from the interface and washed 3 times with HBSS.

To trace these cells, the isolated MNCs were labeled with DiI (CellTracker; Molecular Probes, Invitrogen), according to the manufacturer's instructions. The cells were then suspended in saline or HA at a density of $5 \times 10^7$ cells/ml, and a total of 2 ml was injected into the animals. Flow cytometry was used to verify the viability of cells after propidium iodide staining and to determine the DiI labeling efficiency. The cells were about 95% viable, with or without embedded in HA, while the DiI labeling efficiency was confirmed to be about 85%.

Myocardial Infarction Disease Model and Treatment

All of the procedures were blinded and randomized. The MI model was created by coronary artery ligation, followed with intra-myocardial injection of therapeutics. For the rat study, 40 rats were divided into 5 groups—sham, MI only, MI with treatment of HA alone, MNC alone ($1 \times 10^6$ MNC in 100 µL PBS), and HA with MNCs ($1 \times 10^6$ MNC in 100 µL HA, n=8). In the cardiomyocyte apoptosis experiment, another 30 rats were divided into 5 groups—sham, MI only, MI with treatment of HA alone, MNC alone ($1 \times 10^6$ MNC in 100 µL PBS), and HA with MNCs ($1 \times 10^6$ MNC in 100 µL HA, n=6). For the pig study, a total of 40 surviving animals were divided into 5 groups—sham operation, which was performed by opening the chest without coronary artery ligation (sham), permanent mid-left anterior descending (LAD) coronary artery ligation (for simulating MI) immediately followed by injection of 2 ml normal saline (MI+NS) or 1% HA solution (MI+HA), MI immediately followed by a 2 ml injection of $10^8$ autologous MNCs suspended in NS (MI+MNCs) or mixed with HA (MI+HA/MNCs). Treatments were injected into the entire infarcted area divided amongst 40 delivery sites (about 50 µL for each site).

Echocardiography

For rats, heart function was evaluated by echocardiography (17 MHz probe, VisualSonics Vevo 770, Toronto, Canada) 1 and 28 days after surgery. For pigs, echocardiography was performed immediately before, immediately after, and 8 weeks after surgery using Vivid 7 with a 3.5 MHz probe (GE Healthcare, Horten, Norway). The animals were placed in the left lateral decubitus position. The anesthesia condition during echocardiography was the same as that during surgery. Parasternal long-axis views were obtained with both M-mode and 2D echo images. Left ventricular end-diastolic diameter (LVEDD) and end-systolic diameter (LVESD) were measured perpendicular to the long axis of the ventricle at the location of the papillary muscle insertion site. Left ventricle ejection fraction (LVEF) was calculated automatically by the echocardiography system as (LVEDV−LVESV)/LVEDV×100%, where LVEDV is the left ventricular end diastolic volume calculated as 7.0×LVEDD3/(2.4+LVEDD) and LVESV is the left ventricle end systolic volume calculated as 7.0×LVESD3/(2.4+LVESD).

Hemodynamics

At 8 weeks after pig surgery, the hemodynamics were assessed by catheterization immediately after echocardiography, using 5.0 Fr. pressure-volume sensing catheters (Millar Instruments, Houston, Tex.). Ten milliliters of blood was drawn from the right jugular vein to calibrate the electrical conductivity for volume conversion and later preserved in EDTA blood collection tubes (Vacutainer™; BD) for further hematologic analysis. The catheter was inserted into the right carotid artery and advanced to the left ventricle (LV). After stabilization, baseline LV pressure-volume loops were recorded. To change preload, the inferior vena cava was transiently compressed through an incision in the upper abdomen. At the end of each catheterization, 10 ml of 25% saline was injected into the right atrium through the right jugular vein to determine the conductance. The volume calibration and the hemodynamic data were analyzed with commercial software (PVAN3.2; Millar Instruments).

Immunofluorescence and Massion Trichrome Staining

The heart was harvested and fixed with 4% paraformaldehyde at 4° C. overnight, then dehydrated and paraffin-embedded. Tissue was then sectioned, deparaffined, and rehydrated. All of the samples were boiled with sodium citrate buffer (pH 6) for antigen retrieval. The sections were incubated with anti-smooth muscle 22 alpha (1:200, Abcam, Cambridge, Mass.), anti-isolectin IB4 (1:100, Invitrogen), anti-troponin I (1:200, DSHB) or anti-vWF (1:50, EMD Millipore, Billerica, Mass.) antibodies at 4° C. overnight. After washing for 3 times, sections were incubated with secondary antibody Alexa Fluor® 488 or 568 (1:200, Invitrogen). The scar tissue was stained by Massion trichrome staining (Sigma-Aldrich), and the images were collected with TissueGnostics GmbH FACS-like tissue cytometry (TissueGnostics GmbH, Vienna, Austria) and t analyzed by ImageJ software.

Statistical Analysis

All measurements are presented as mean±standard deviation. Statistical significance was estimated using one-way or two-way ANOVA. A value of P<0.05 is considered statistically significant.

EXPERIMENTS

Effect of HA on Bone Marrow MNC Adhesion and Proliferation

As the bone marrow MNCs were a population with mixed cell types, most of the cells were suspended cells during in vitro culture. Since the binding ability of cells is an important issue for cell delivery and cell retention in a transplanted region, the effect of HA on bone marrow MNCs was studied in vitro. To test if HA improves the adhesion ability of bone marrow MNCs, total bone marrow cells were isolated, and then purified MNCs were obtained by gradient centrifuge. The MNCs were then seeded onto different materials, including fibronectin and gelatin, which are commonly used in cell culture to favor cell adhesion. The number of adherent cells was significantly increased after 60 minutes in the HA coated group compared to the control, fibronectin and gelatin coated groups (**P<0.01; FIG. 1A). Thus, HA increases MNCs adhesion and ability to bind various materials.

Figure 1B:
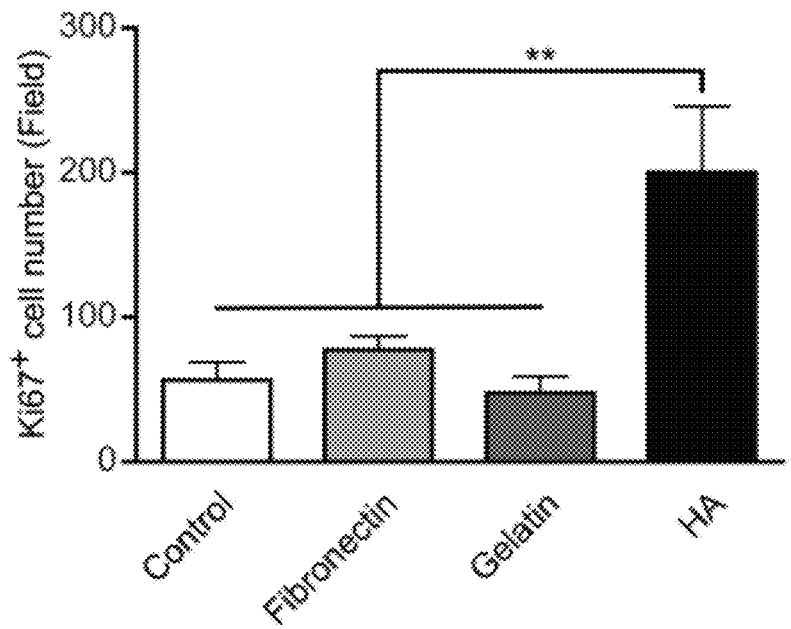

To determine whether the cell cycle of the adherent MNCs was affected, the cells were cultured for 24 hours and stained with the proliferation maker Ki67. Quantification results show that HA increases cell proliferation (**P<0.01; FIG. 1B). Thus, HA promotes both adhesion and proliferation of MNCs. Therefore, in some embodiments, the present invention is directed to methods of increasing the adhesion and/or proliferation of MNCs administering HA to the MNCs.

Figure 2A:
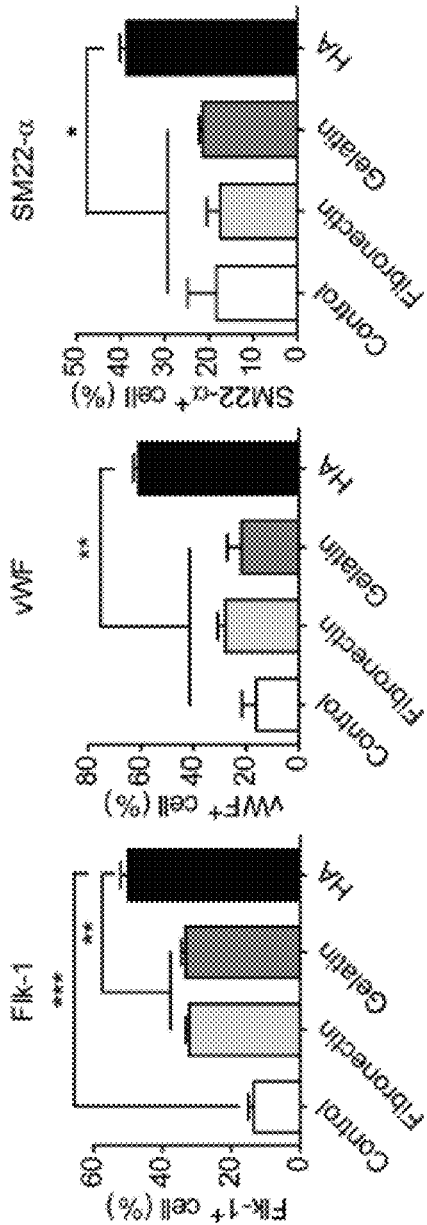
FIGS. 2A-2C show that HA promotes MNC differentiation, angiogenic gene expression and survival.

HA Modulated Bone Marrow MNC Differentiation and Promoted Paracrine Factor Secretion and Anti-Apoptosis Bone marrow MNCs contain several kinds of progenitor cells as well as the ability to generate various cell types including vascular lineage cells, which is important for angiogenesis in ischemia diseases. To examine whether different coating conditions affects differentiation of vascular lineaged cells from MNCs, MNCs which were cultured in endothelial basal medium were stained with a mature endothelial cell marker—Von willebrand factor (vWF), a smooth muscle cell marker—smooth 22 alpha (SM22-α), and an endothelial progenitor cell marker—fetal liver kinase 1 (Flk-1). The results revealed that the attached MNCs are capable of differentiating into vascular lineage cells such as smooth muscle cells and endothelial cells. Moreover, some small Flk-1$^+$ colonies were observed 4 days after plating (FIG. 2A), which may represent the endothelial progenitor cell population. Quantification results indicate that HA coating significantly improves differentiation of vascular lineage cells from MNCs (*P<0.05, P<0.01, *P<0.001, FIG. 2A). Therefore, in some embodiments, the present invention is directed to improving the differentiation of MNCs which comprises administering HA to the MNCs.

Figure 2B:
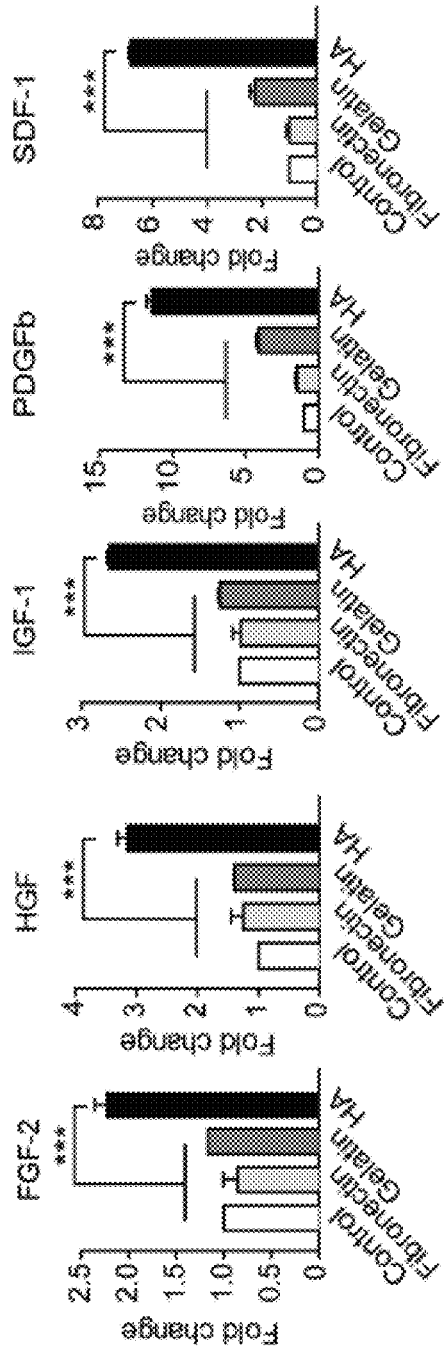
Figure 2C:
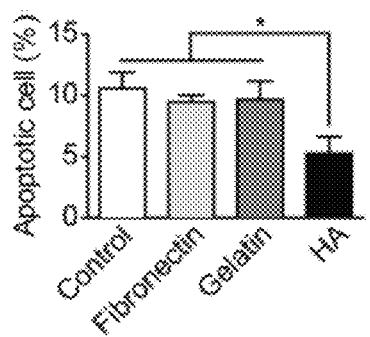

These observations indicate that part of the MNCs differentiate into vascular lineage cells, while other cells may play a different role. Therefore, the effect of HA on angiogenic and anti-apoptotic factor secretion was examined. The MNCs were cultured in different coating materials under hypoxia conditions which mimic the ischemia condition in vivo for 2 days and then gene expression analysis was conducted. The expression of genes that were analyzed and quantified included fibroblast growth factor-2 (FGF-2), hepatocyte growth factor (HGF), insulin-like growth factor (IGF), platelet-derived growth factor subunit b (PDGFb), and stromal cell-derived factor-1 (SDF-1). The results indicate that HA can significantly elevate the expression level of paracrine factor genes at day 2 (P<0.001; FIG. 2B). Next, doxorubicin was used to induce apoptosis of MNCs. It was found that the apoptotic cell number was reduced in the HA group as compared to the other experimental groups (FIG. 2C, *P<0.05). Therefore, in some embodiments, the present invention is directed to reducing apoptosis of cells which comprises administering HA to the cells. In some embodiments, the cells are MNCs.

HA/MNC Injection Reduced Cardiomyocyte Death In Vivo

Figure 3:
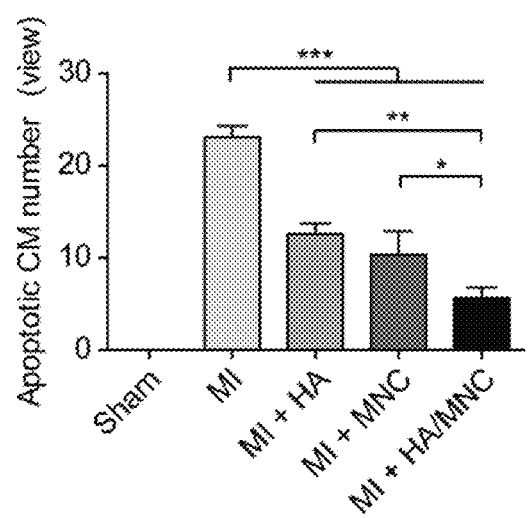
FIG. 3 shows that treatment with both HA and MNC (HA/MNC treatment) reduces cardiomyocyte apoptosis following myocardial infarction in rats. The reduced fold changes of cardiomyocyte apoptosis by HA/MNC treatment are as follows: 4.1× vs. control, 2.1× vs. HA alone and 1.8× vs. MNC alone. Data are mean±SEM. *$P<0.05$, $P<0.01$, *$P<0.001$. n=6 per group.

The in vitro data herein suggests that HA can promote MNC adhesion and proliferation. Moreover, HA regulates MNC differentiation and provides an anti-apoptotic effect. To further understand the effect of HA/MNC injection in vivo, coronary artery ligation surgery to block the blood flow in myocardium was performed and then HA or MNC alone or HA combined with MNC was injected into the ischemic heart. One day post-MI, the hearts were harvested and TUNEL staining was used to confirm the number of cardiomyocytes undergoing apoptosis. The TUNEL assay showed that there were fewer apoptotic cardiomyocytes in the HA/MNC group one day after MI (***P<0.001, FIG. 3). Therefore, in some embodiments, the present invention is directed to reducing the number of apoptopic cardiomyocytes in a subject which comprises administering HA and MNCs to the cardiomyocytes in the subject. In some embodiments, the cardiomyocytes are of an ischemic heart, i.e., the subject suffers from ischemia. In some embodiments, the HA and MNCs are injected directly into one or more cardiac tissues of the subject.

Combined HA/MNC Treatment Reduced Inflammatory Response after MI

Figure 4A:
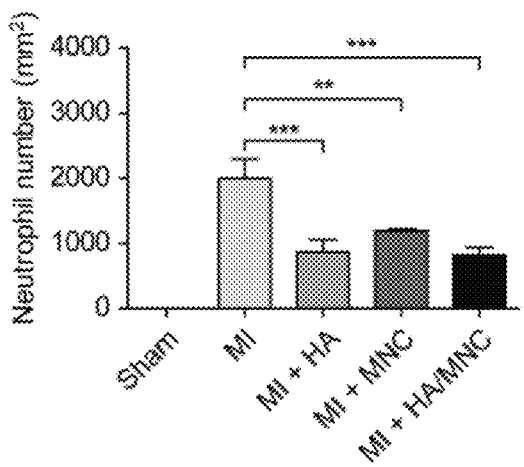
FIGS. 4A-4B show that HA/MNC treatment decreases neutrophil and macrophage infiltration after infarction in rats.
Figure 4B:
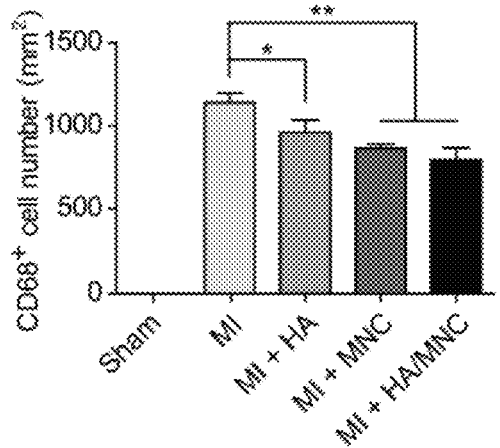

Inflammation is part of the healing process after MI. However, strong and regional inflammation may damage myocytes and enlarge the size of scar tissue, resulting in changes in long term prognosis. To determine if the combination of HA and MNCs modulates the inflammatory response, the number of infiltrated neutrophil and macrophage in peri-infarct region was quantified by HE staining and IHC staining of CD68 (macrophage specific antigen), respectively. Interestingly, the injection of HA and HA/MNC reduced neutrophil infiltration in the peri-infarct region (***P<0.001, FIG. 4A). Furthermore, the number of macrophages was also significantly reduced in the combined treatment group (*P<0.05, **P<0.01, FIG. 4B). Thus, the combination of HA and MNCs reduces the inflammatory response after MI. Therefore, in some embodiments, the present invention is directed to methods of treating or reducing the inflammatory response resulting from MI in a subject which comprises administering to the subject HA and MNCs before, during, or after MI.

Combined HA/MNC Injection Improved Heart Function

Figure 5A:
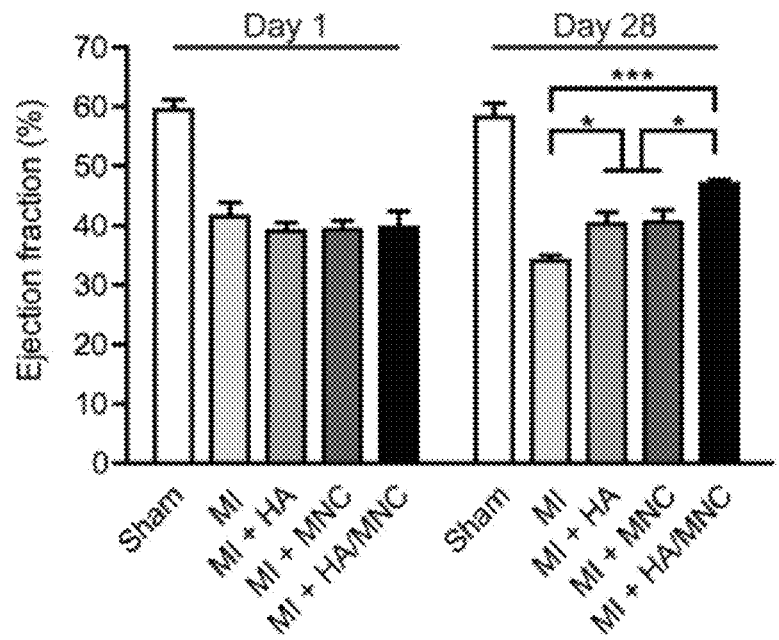
FIGS. 5A-5D show that HA/MNC treatment improves heart performance and reduces scar formation post-MI in rats.
Figure 5B:
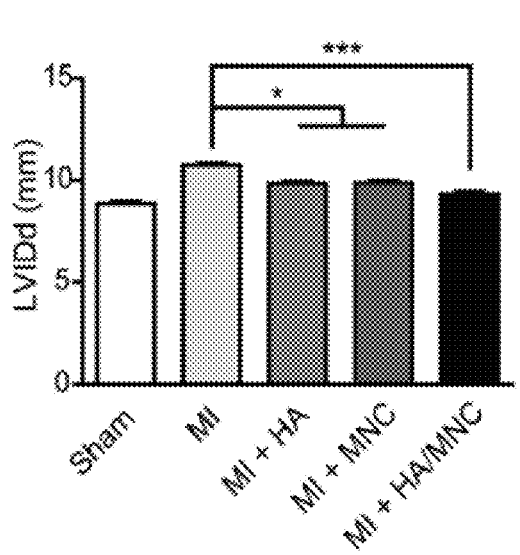
Figure 5C:
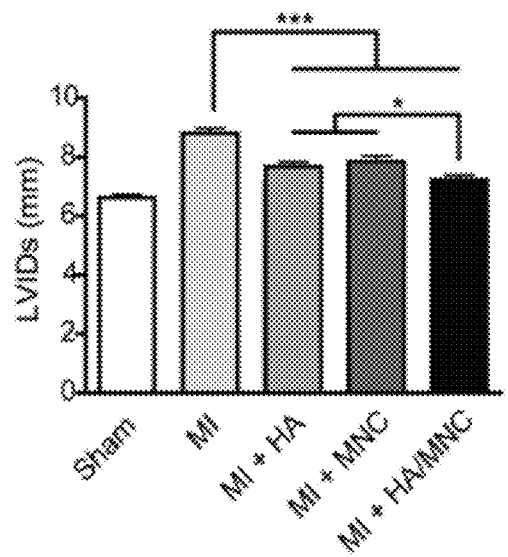
Figure 9A:
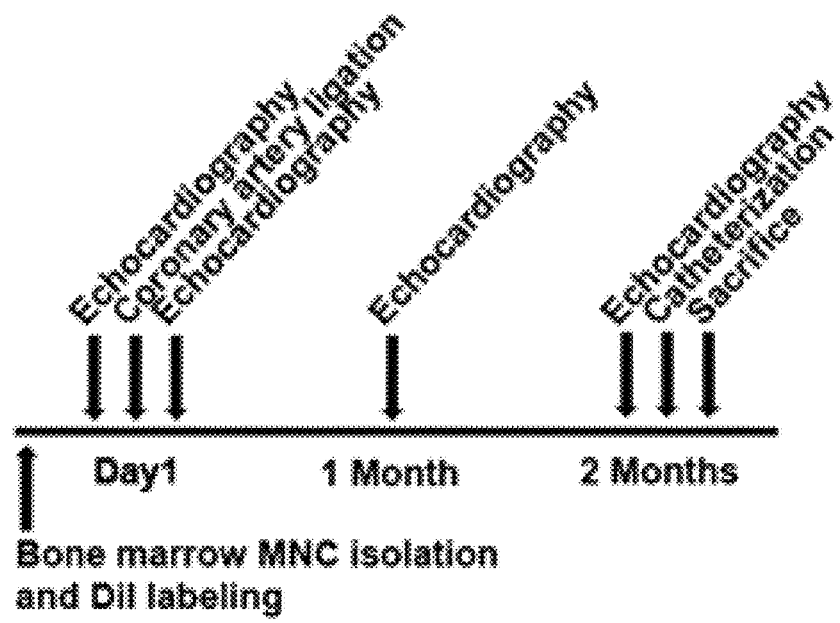
FIGS. 9A-9D show that HA/MNC treatment improves heart performance and enhances diastolic and systolic functions post-MI in pigs.
Figure 9B:
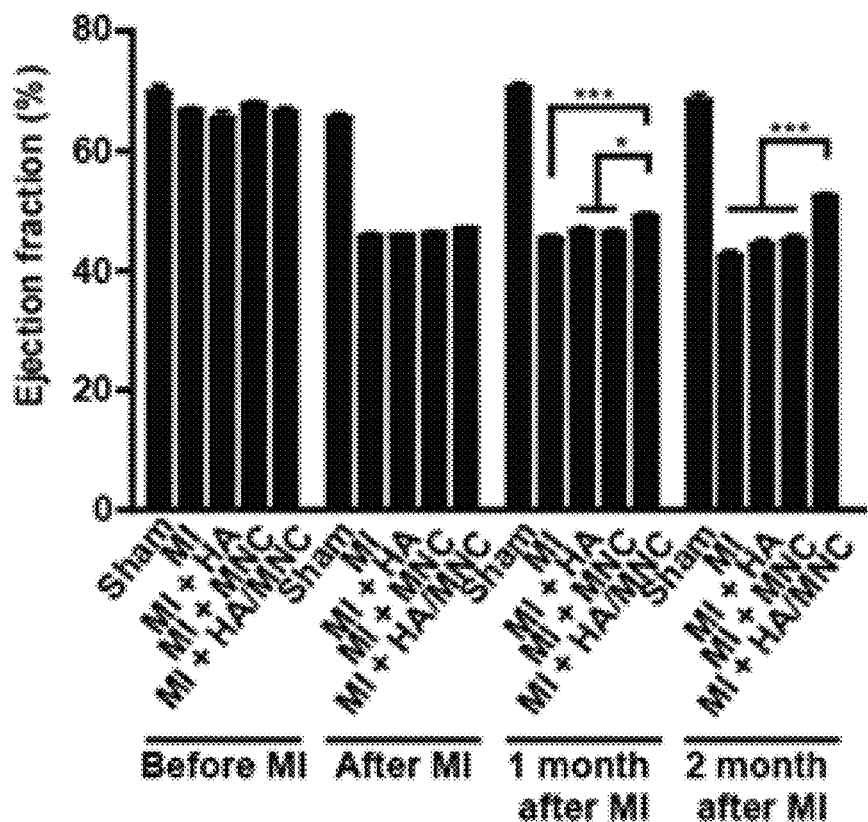
Figure 9C:
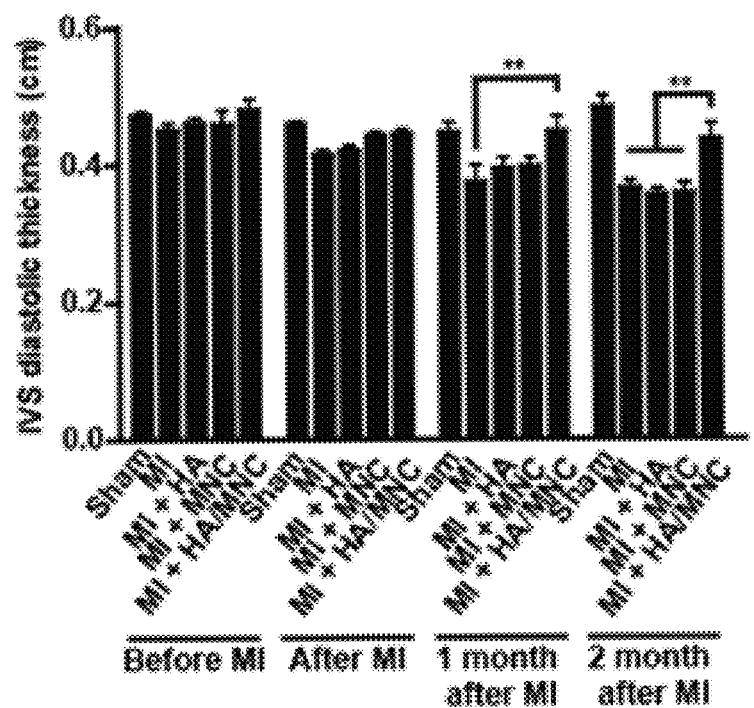
Figure 9D:
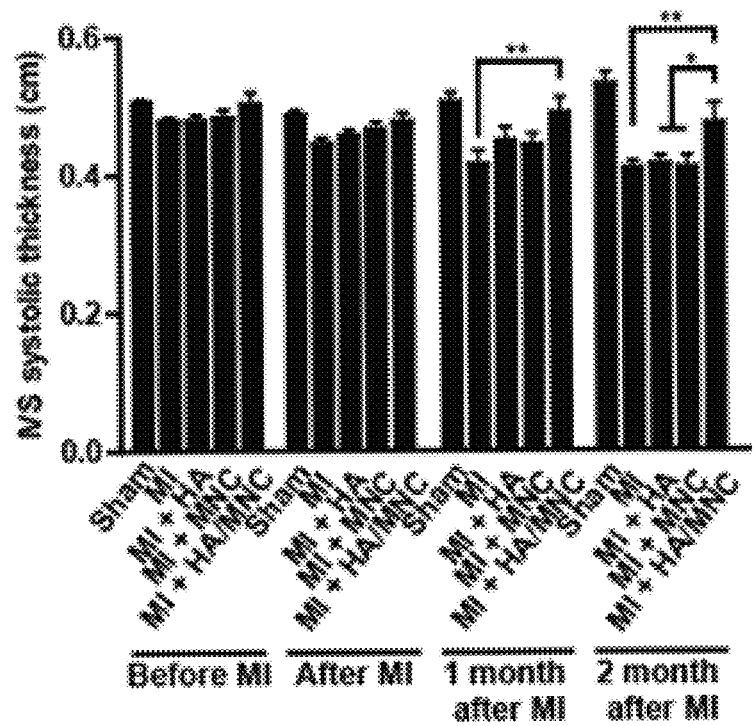

To determine if the combination of HA and MNCs improves the heart function, echocardiography was performed. Although the heart function was slightly improved in the HA treatment group and the MNC treatment group, the combination of HA and MNCs significantly increased the ejection fraction 28 days in rats and pigs and 56 days in pigs post-MI (*$P<0.05$, $P<0.01$, *$P<0.001$, FIGS. 5A and 9B). Consistent with this finding, the systolic and diastolic functions were also improved in the HA, MNC alone and HA/MNC group (*$P<0.05$, *$P<0.001$, FIGS. 5B-5C and 9C-9D**). Therefore, in some embodiments, the present invention is directed to improving the function of a subject's heart after MI which comprises administering HA and MNCs to the heart. In some embodiments, the HA and MNCs are injected directly into one or more cardiac tissues of the subject.

Scar Formation was Decreased after HA/MNC Injection

Figure 5D:
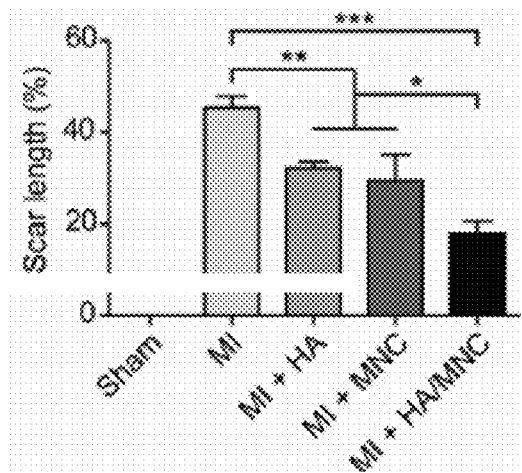
Figure 6:
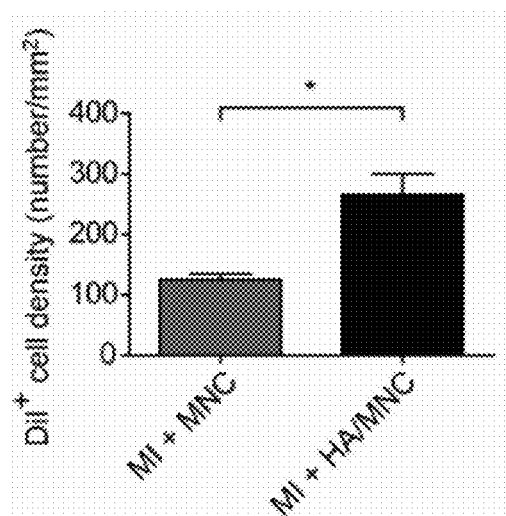
FIG. 6 shows that HA/MNC treatment improves transplanted cell retention after MI in rats. The cell retention rates are reflected by DiI$^+$ cell counts. The data are presented as the mean±SEM. *$P<0.05$. n=8 per group. HA/MNC treatment increases about 2.1-fold more cells retained in the rat heart compared with treatment with MNC alone.
Figure 10A:
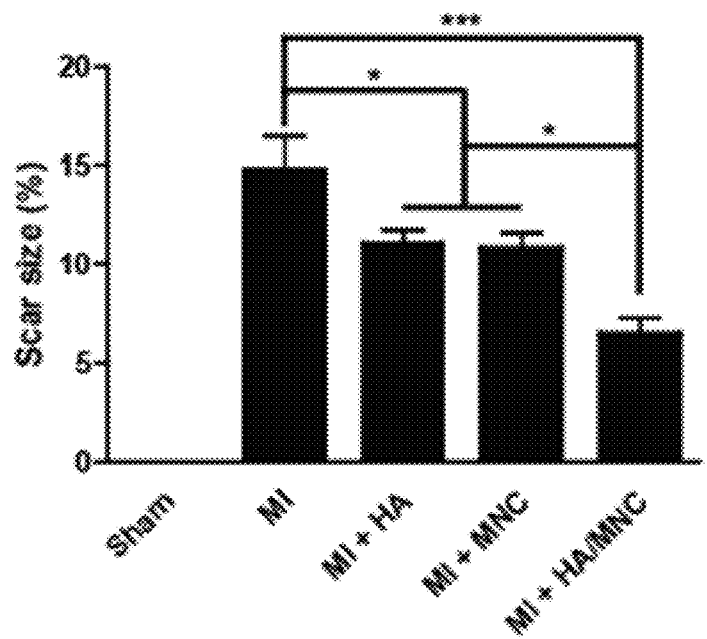
FIGS. 10A-10C show that HA/MNC treatment reduces scar formation and increases wall thickness post-MI in pigs. The percentage of scar size (FIG. 10A), scar length (FIG. 10B), and interventricular wall thickness (FIG. 10C) were calculated using computer image software. Data are presented as mean±SEM. *P<0.05, P<0.01, *P<0.001. n=7 per group. HA/MNC treatment exerts less scar size (about 6%) than those in control (14%), HA alone (11%) or MNC alone (10%) group and less scar length (about 14%) than those in control (26%), HA alone (21%) or MNC alone (20%) group, and larger wall thickness (about 88%) than those in control (53%), HA alone (70%) or MNC alone (66%) group.
Figure 10B:
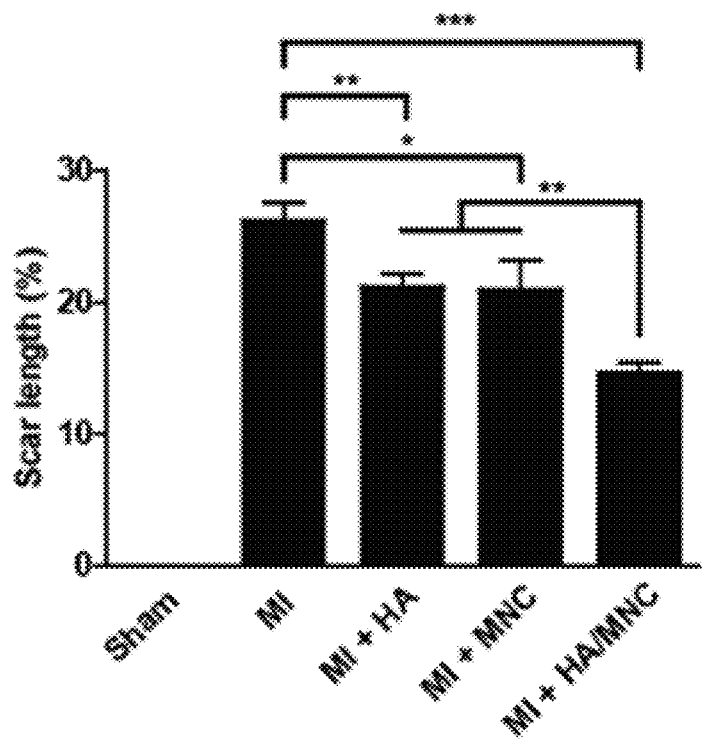
Figure 10C:
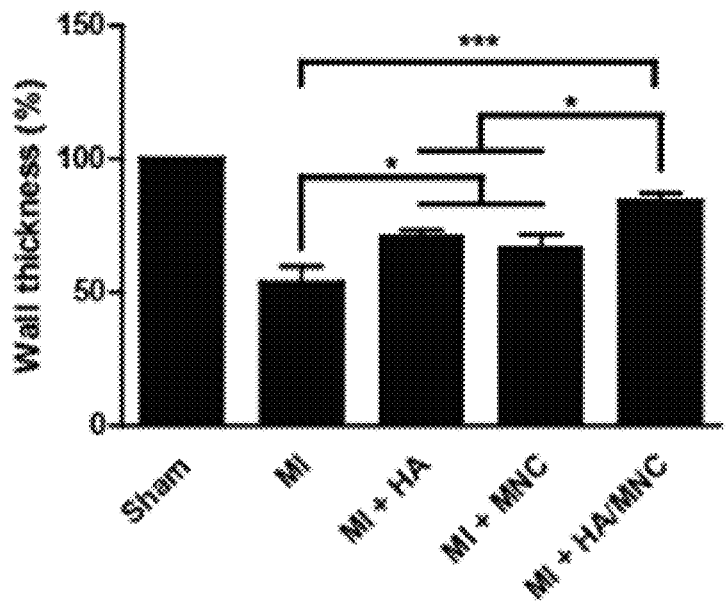
Figure 11:
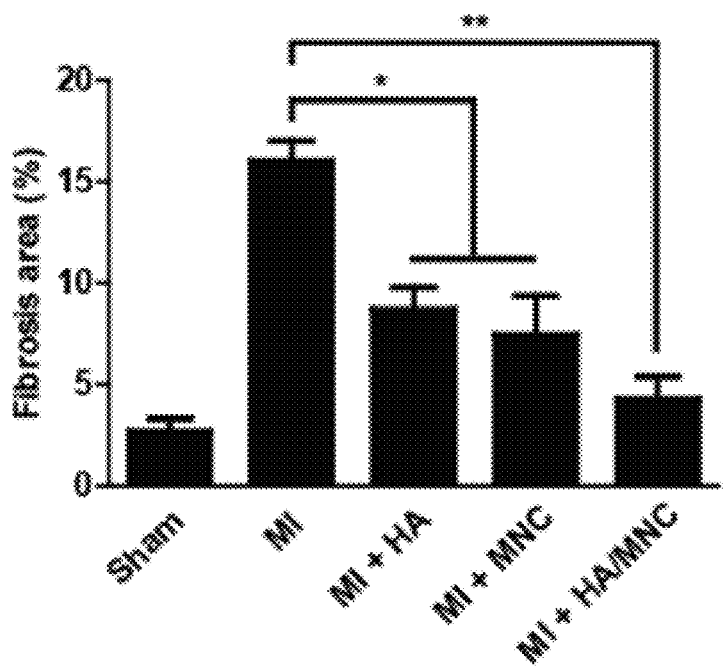
FIG. 11 shows that HA/MNC treatment reduces collagen accumulation at the remote area post-MI in pigs. The statistical analysis of collagen deposition at the non-infarct remote area from various groups is presented as the mean±SEM. *P<0.05, **P<0.01. n=7 per group. HA/MNC treatment significantly reduces the fibrosis area (about 4.6%) compared with control (16.1%) or HA alone (9.0%) or MNC alone (7.6%) treatment.
Figure 12:
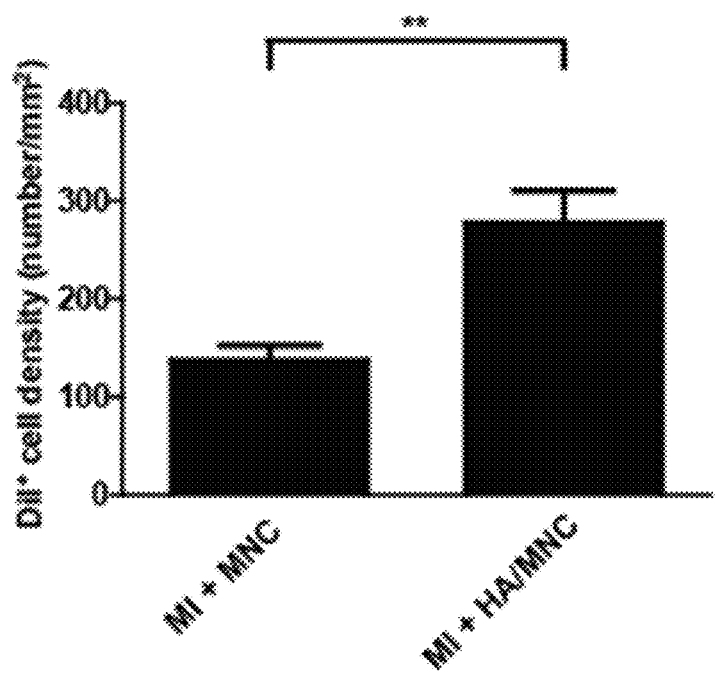
FIG. 12 shows that HA/MNC treatment improves transplanted cell retention post-MI in pigs. The cell retention rates are reflected by DiI$^+$ cell counts. The data are presented as the mean±SEM. *P<0.05. n=7 per group. HA/MNC treatment increases about 2-fold more cells retained in the pig heart compared with treatment with MNC alone.

To determine if the improvement in the cardiac function is accompanied with a reduction in scar size, Masson trichrome staining was used to measure the scar length (FIGS. 5D and 10). It was found that the size of scar tissue decreased in both HA and MNC groups. Remarkably, the scar tissue and collagen accumulation were further minimized in the HA/MNC combined treatment group (*$P<0.05$, $P<0.01$, *$P<0.001$, FIGS. 5D, 10, and 11). On the basis of this finding, it was speculated that HA/MNC combined treatment may modulate scar tissue size by reducing cardiomyocyte death. The injected MNCs which were retained 28 days post-MI were quantified. It was found that the HA/MNC group had significantly more MNCs retained in the ischemic heart 28 days in rats (*$P<0.05$, FIG. 6) and 56 days in pigs after MI ($P<0.01$, FIG. 12**). Therefore, in some embodiments, the present invention is directed to reducing scar tissue formation and/or collagen accumulation in one or more cardiac tissues of a subject after MI which comprises administering HA and MNCs to the subject. In some embodiments, the HA and MNCs are injected directly into one or more cardiac tissues of the subject.

HA/MNC Injection Promoted Angiogenesis

Figure 7A:
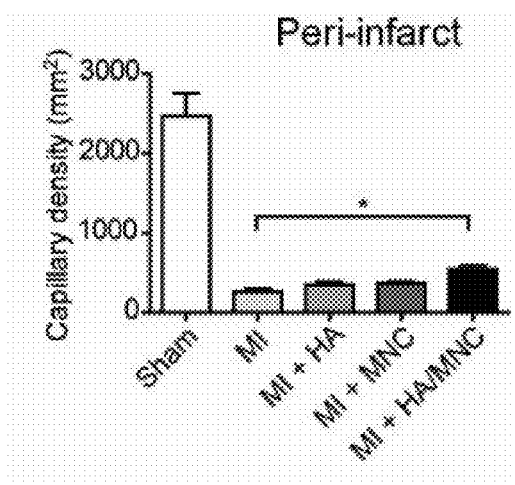
FIGS. 7A-7D show that HA/MNC treatment increases capillary and arteriole densities post-MI in rats.
Figure 7B:
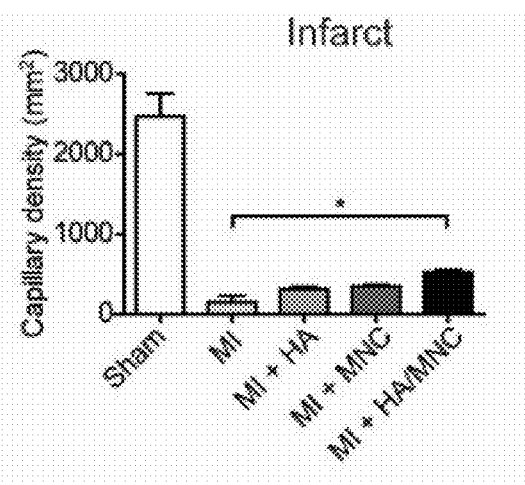
Figure 13A:
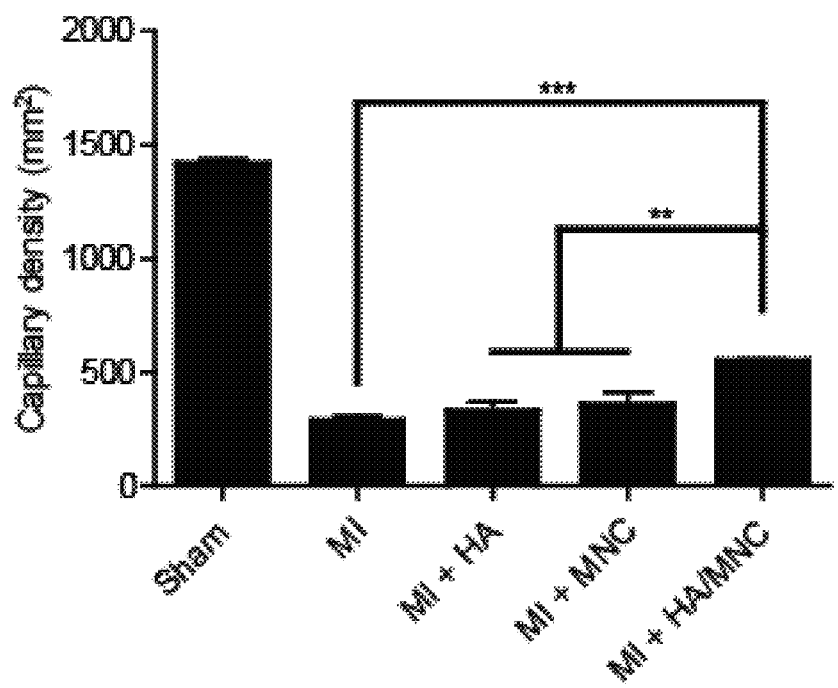
FIGS. 13A-13B show that HA/MNC treatment increases capillary and arteriole densities post-MI in pigs. The quantification of capillary (FIG. 13A, P<0.01, *P<0.001) and arteriole (FIG. 13B, *P<0.05, **P<0.01) densities at the peri-infarct area are presented as the mean±SEM. n=7 per group. Compared with control, HA/MNC treatment improves capillary density by about 1.9 fold and arteriole density by about 1.8 fold.
Figure 13B:
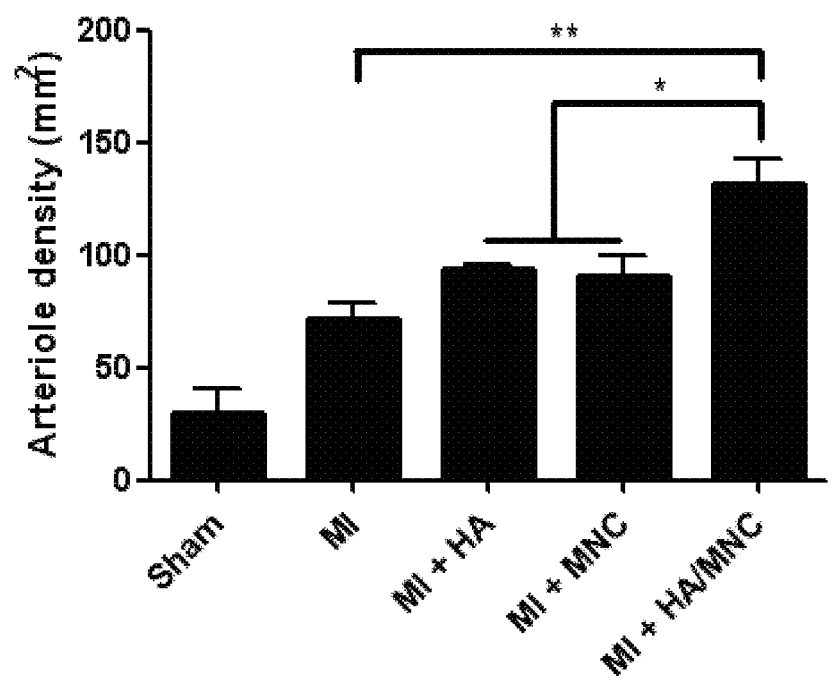

As HA/MNC injection reduces scar length after MI, whether the HA/MNC combined treatment promotes angiogenesis in the ischemic heart was investigated. IHC staining of the endothelial marker isolectin was performed and the capillary density in peri-infarct and infarct region was quantified (FIGS. 7A and 13A). The results show that the capillary density of HA and MNC group was only slightly increased; however, injection of HA/MNC significantly enhanced capillary density in both the peri-infarct and infarct region (*$P<0.05$, $P<0.01$, *$P<0.001$, FIGS. 7A, 13A, and 13B). Thus, the combination of HA and MNCs promotes angiogenesis. Therefore, in some embodiments, the present invention is directed to promoting and/or increasing angiogenesis in a subject which comprises administering HA and MNCs to the subject. In some embodiments, the HA and MNCs are injected directly into one or more cardiac tissues of the subject. In some embodiments, the HA and MNCs are administered before, during, or after MI.

HA/MNC Injection Promoted Arteriogenesis

Figure 7C:
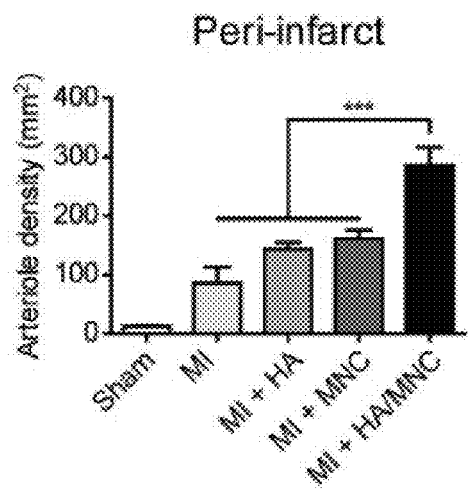
Figure 7D:
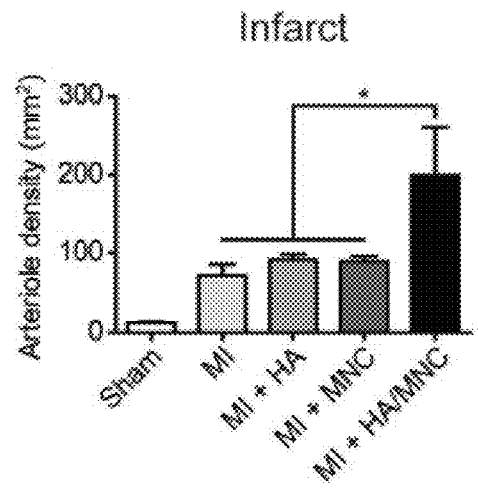

The smooth muscle cells are important for stabilizing de novo formation of blood vessel (Jain, R K (2003) Molecular regulation of vessel maturation. Nat Med 9: 685-693). Therefore, the cells were stained with smooth muscle 22 alpha (SM22-α) to examine the degree of arteriogenesis. Quantification results indicate that arteriole density in the HA/MNC treatment group was significantly increased as compared with other experimental groups (*$P<0.05$, $P<0.01$, *$P<0.001$, FIG. 7C-7D, 13B).

Therefore, in some embodiments, the present invention is directed to promoting and/or increasing arteriogenesis in a subject which comprises administering HA and MNCs to the subject. In some embodiments, the HA and MNCs are injected directly into one or more cardiac tissues of the subject. In some embodiments, the HA and MNCs are administered before, during, or after MI.

HA/MNC Injection Improved Vascular Integration

Figure 8:
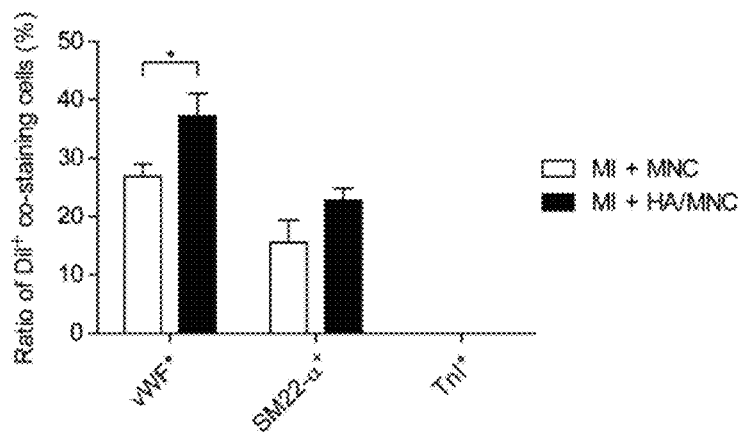
FIG. 8 shows that HA/MNC treatment enhances transplanted cell differentiation into vascular cells but not cardiomyocytes. Quantification of ratio of cells double positive with DiI and vWF, SM22-α or TnI. *P<0.05. Data shows that HA/MNC treatment increases both endothelial cell and vascular smooth muscle cell differentiation by about 1.4× compared with treatment with MNC alone.

To investigate the cell fate of MNCs, the cells were stained with SM22-α or vWF with DiI. DiI/SM22-α and DiI/vWF double positive cells were detected and were found to integrate into the pre-existing vessels, thereby suggesting that transplanted MNCs contribute to post-MI neovascularisation (FIG. 8).

Therefore, in some embodiments, the present invention is directed to promoting and/or increasing MNC vascular integration in a subject which comprises administering HA and the MNCs to the subject. In some embodiments, the HA and MNCs are injected directly into one or more cardiac tissues of the subject. In some embodiments, the HA and MNCs are administered before, during, or after MI.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method for treating a cardiovascular disease or damaged cardiac tissue in a subject comprising:
    administering to the myocardium of the subject at least one hyaluronan (HA) compound and one or more cells selected from the group consisting of stem cells, precursor cells, progenitor cells, committed cells, mature somatic cells, and recombinant cells,
    wherein the molecular weight of the HA is less than 1500 kDa, the amount of the at least one HA compound is about 0.01 to about 10 mg/kg body weight of the subject, the amount of the one or more cells is about $1 \times 10^4$ to about $1 \times 10^8$ cell/kg body weight of the subject and the HA provides therapeutic effects comprising promotion of proliferation of the one or more cells and promotion of angiogenesis.

2. The method of claim 1, wherein the cardiovascular disease is coronary artery disease, cardiomyopathy, myocardial infarction, atherosclerosis, heart failure, a congenital heart disease, a valvular heart disease, or a vascular disease.

3. The method of claim 2, wherein the vascular disease is any of peripheral artery occlusive disease, Raynaud's phenomenon, Berger's disease, or vascular inflammation or damage.

4. The method of claim 1, wherein the damaged cardiac tissue was caused by a trauma thereto or a viral infection.

5. The method of claim 1, wherein the at least one HA compound and the one or more cells are administered to the subject before, during, and/or after the occurrence of the cardiovascular disease or damage to the cardiac tissue.

6. The method of claim 5, wherein the at least one HA compound and the one or more cells are administered together in the form of a single composition.

7. The method of claim 1, wherein the one or more cells are hematopoietic stem cells, mesenchymal stem cells, endothelial stem cells, and/or blood cells.

8. The method of claim 1, wherein the one or more cells are autologous cells to the subject or allogeneic cells from one or more donors.

9. The method of claim 1, wherein the one or more cells are myofibroblasts, bone marrow cells, blood cells, adipose tissue-derived cells, placental cells, umbilical cord cells, umbilical cord blood cells, amniotic fluid cells, cardiomyocyte-like cells, pluripotent stem cell-derived cells, or somatic cell-derived stem/progenitor cells.

10. The method of claim 1, wherein the at least one HA compound and the one or more cells are administered to the myocardium of a heart by thoracotomy, cardiac catheterization, echo-guided or endoscope-assisted injection, or a syringe.

11. The method of claim 1, wherein the HA further provides one or more therapeutic effects selected from the group consisting of comprising promotion of mononuclear cell (MNC) differentiation, promotion of angiogenic gene expression, promotion of cell survival, reduction of inflammation, improvement in cardiac protection, improvement in cardiac function and/or reduction of scar tissue formation and collagen accumulation in cardiac tissues.

* * * * *